(12) United States Patent
Monteiro de Barros Carneiro et al.

(10) Patent No.: US 8,556,814 B2
(45) Date of Patent: Oct. 15, 2013

(54) AUTOMATED FETAL MEASUREMENT FROM THREE-DIMENSIONAL ULTRASOUND DATA

(75) Inventors: Gustavo Henrique Monteiro de Barros Carneiro, Lisbon (PT); Fernando Amat, San Francisco, CA (US); Bogdan Georgescu, Plainsboro, NJ (US); Sara Good, Pleasanton, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1306 days.

(21) Appl. No.: 12/239,898

(22) Filed: Sep. 29, 2008

(65) Prior Publication Data

US 2009/0093717 A1    Apr. 9, 2009

Related U.S. Application Data

(60) Provisional application No. 60/977,494, filed on Oct. 4, 2007.

(51) Int. Cl.
*A61B 8/00*    (2006.01)

(52) U.S. Cl.
USPC ........... 600/443; 600/437; 128/922; 128/925; 706/14; 706/16

(58) Field of Classification Search
USPC ........ 600/437, 443; 128/922, 925; 706/14, 16
See application file for complete search history.

(56) References Cited

U.S. PATENT DOCUMENTS

| | | | |
|---|---|---|---|
| 5,655,535 A * | 8/1997 | Friemel et al. | 600/443 |
| 6,720,966 B2 * | 4/2004 | Barth et al. | 345/424 |
| 7,783,095 B2 * | 8/2010 | Carneiro et al. | 382/128 |
| 7,889,898 B2 | 2/2011 | Chakraborty et al. | |
| 7,995,820 B2 * | 8/2011 | de Barros Carneiro et al. | 382/128 |
| 2004/0147840 A1 * | 7/2004 | Duggirala et al. | 600/437 |
| 2006/0122506 A1 * | 6/2006 | Davies et al. | 600/437 |

OTHER PUBLICATIONS

Beryl R. Benacerraf, Thomas D. Shipp, and Bryann Bromley, "How Sonographic Tomography Will Change the Face of Obstetric Sonography: A Pilot Study", J. Ultrasound Med., Mar. 2005., vol. 24:3, pp. 371-378.

P. Viola, M.J. Jones, Robust Real-Time Face Detection, International Journal of Computer Vision 57(2), 137-154, 2004.

M. Sabry Hassouna and Aly A. Farag, "Roust Centerline Extraction Framework Using Level Sets", IEEE Int. Conference on Computer Vision and Pattern Recognition, 2005.

Hadlock F.P., Deter R.L, Harrist R.B., Park S.K., "Estimating fetal age: computer-assisted analysis of multiple fetal growth parameters," Radiology Aug. 1984 152(2): 497-401.

(Continued)

*Primary Examiner* — Unsu Jung
*Assistant Examiner* — Joseph M Santos Rodriguez

(57) ABSTRACT

A fetal parameter or anatomy is measured or detected from three-dimensional ultrasound data. An algorithm is machine-trained to detect fetal anatomy. Any machine training approach may be used. The machine-trained classifier is a joint classifier, such that one anatomy is detected using the ultrasound data and the detected location of another anatomy. The machine-trained classifier uses marginal space such that the location of anatomy is detected sequentially through translation, orientation and scale rather than detecting for all location parameters at once. The machine-trained classifier includes detectors for detecting from the ultrasound data at different resolutions, such as in a pyramid volume.

15 Claims, 2 Drawing Sheets

(56) References Cited

OTHER PUBLICATIONS

Westerway SC, Davison A. Cowell S, "Ultrasonic fetal measurements: new Australian standards for the new millennium", Aust NZJ Obstet Gynaecol Aug. 2000 40(3): 297-302.
Necas M., "Musculoskeletal symptomatology and repetitive strain injuries in diagnostic medical sonographers: A pilot study in Washington and Oregon," Journal of Diagnostic Medical Sonography, 12: 266-273, 1996.
Pike I, Russo A, Berkowtiz J, Baker J, Lessoway VA., "The Prevalence of Musculoskeletal Disorders Among Diagnostic Medical Sonographers," Journal of Diagnostic Medical Sonography, 13: 219-227, Sep./Oct. 1997.
The International Society of Ultrasound in Obstetrics and Gynecology, "Sonographic Examination of the Fetal Central Nervous System: Guidelines for Performing the Basic Examination of the Fetal Central Nervous System: Guidelines for Performing the Basic Examination and the Fetal Neurosonogram". Ultrasound in Obstetrics and Gynecology, 29: 109-116, 2007.
Z.Tu "Probabilistic Boosting-Tree: Learning Discriminative Models for Classification, Recognition, and Clustering". Proc. *International Conference on Computer Vision*, pp. 1589-1596 (2005).
G. Carneiro and D. Lowe, Sparse flexible models of local features. ECCV, 2006.
F.F.Correa, C. Lara, J Bellver, J. Remoh, A. Pellicer, and V. Serra. Examination of the fetal brain by transabdominal three-dimensional ultrasound: potential for routine neurosonographic studies. *Ultrasound in Obstetrics and Gynecology*, 27(5): 503-508, 2006.
B. Benacerraf et al., Three- and 4-dimensional ultrasound in obstetrics and gynecology—proceedings of the American institute of ultrasound in medicine consensus conference. *J. Ultrasound Med*, 24: 1587-1597, 2005.
M. Gooding, S. Kennedy, and J.A. Noble. Volume reconstruction from sparse 3d ultrasonography. MICCAI, 2003.
W. Hong, B. Georgescu, X. Zhou, S. Krishnan, Y. Ma, and D. Comaniciu. Database-guided simultaneous multi-slice 3d segmentation for volumetric data. ECCV, 2006.
A. Johnson and M. Hebert. Using spin images for efficient object recognition in cluttered 3d scenes. IEEE TPAMI, 21(5), 1999.
C. F. F. Karney. Quaternions in molecular modeling J.Mol.Graph. Mod., 25:595-604, 2006.
G. Michailidis, P. Papageorgiou, and D. Economides. Assessment of fetal anatomy in the first trimester using tw0-and three-dimensional ultrasound. *British Journal of Radiology*, 75: 215-219, 2002.
P. Moral, A. Doucet, and G. Peters. Sequential monte carlo samplers. *J. R. Statist. Soc. B*, 68:411436, 2006.
M. Oren, C. Papageorgiou, P. Sinha, E. Osuna, and T. Poggio. Pedestrian detection using wavelet templates. *IEEE CVPR*, 1997.
A. Rabinovich, A. Vedaldi, C. Galleguillos, E. Wiewiora, and S. Belongie. Objects in context. *ICCV*,2007.
R. Rohling, A. Gee, and L. Berman, Automatic registration of 3-d ultrasound images. *ICCV*, pp. 298-303, 1998.
B.H. Romeny, B. Titulaer, S. Kalitzin, G. Scheffer, F. Broekmans, T. Staal, and E. te Velde. Computer assisted human follicle analysis for fertility prospects with 3d ultrasound. *Proceedings of the International Conference on Information Processing in Medical Imaging*, pp. 56-69, 1999.
R. Shekhar and V Zagrodsky. Mutual information-based rigid and nonrigid registration of ultrasound volumes. *IEEE) Transactions on Medical Imaging*, 21(1 ):9-22,2002.
A. Torralba. Contextual priming for object detection. *IJCV*, 53(2):169-191,2003.
Z. Tu, K. Narr, P. Dollar, I. Dinov, P. Thompson, and A. Toga. Brain anatomical structure segmentation by hybrid discriminative/generative models. *Transactions on Medical Imaging*, 2007.
Z. Tu, X. Zhou, D. Comaniciu, and L. Bogoni. A learning based approach for 3d segmentation and colon detagging. *ECCV*, 2006.
P. Viola and M. Jones. Rapid object detection using a boosted cascade of simple features. *CVPR*, pp. 511-518, 2001.
Y. Zheng, A. Barbu, B. Georgescu, M. Scheuering, and D. Comaniciu. Fast automatic heart chamber segmentation from 3d ct data using marginal space learning and steerable features. *ICCV*, 2007.

* cited by examiner

AUTOMATED FETAL MEASUREMENT FROM THREE-DIMENSIONAL ULTRASOUND DATA

RELATED APPLICATIONS

The present patent document claims the benefit of the filing date under 35 U.S.C. §119(e) of Provisional U.S. Patent Application Ser. No. 60/977,494, filed Oct. 4, 2007, which is hereby incorporated by reference.

BACKGROUND

The present embodiments relate to medical diagnostic ultrasound imaging. In particular, fetal measurements are performed using ultrasound data representing a volume.

Fetal biometric measurements represent an important factor for high quality obstetrics health care. Fetal biometric measurements are used for estimating the gestational age (GA) of the fetus, assessing of fetal size, and monitoring of fetal growth and health. To perform the measurements, a physician or sonographer manually searches for a standardized plane using 2-D ultrasound (2DUS) images. Manual searching is cumbersome and contributes to excessive length in clinical obstetric examinations. Long ultrasound examinations may lead to increased costs.

Three-dimensional ultrasound (3DUS) data may have increasing importance in radiology for fetal diagnosis. Compared to 2DUS, the main advantages of 3D US may include a substantial decrease in the examination time, a possibility of post-exam data processing without requesting additional visits of the patient, and the ability of experts to produce 2-D views of the fetal anatomies in orientations that cannot be seen in common 2-D ultrasound exams. However, extensive manipulation on the part of the physician or the sonographer may be required in order to identify standard planes for measurements from the 3DUS data. The learning curve to understand these manipulation steps is quite large, even for expert users. Usually, expert users find several landmarks in order to reach the sought anatomy. For example, the standardized plane for measuring the lateral ventricles in the fetus brain is referred to as the transventricular plane. The user searches for the cavum septi pellucidi, frontal horn, atrium, and choroids plexus in order to identify the plane. Since the fetus is oriented in an arbitrary position in each volume, an expert sonographer may require several minutes to localize the structures in a basic examination.

Some automated or semi-automated processes may be used to assist in 3DUS. In the field of 3DUS, segmentation and registration of specific anatomical structures may be provided. However, segmentation and registration merely separate data representing an already identified structure.

In computer vision, there are methods for recognizing 3D objects using range images, but these applications are different in the sense that the system works with surfaces instead of actual volumes. Using 3-D magnetic resonance imaging (3DMRI) data, a combination of a discriminant classifier based on the probabilistic boosting tree (PBD) for appearance and generative classifier based on principal components analysis (PCA) for shape, where the weights for these two terms are learned automatically, has been proposed. This is applied to the segmentation of eight brain structures, where the system takes eight minutes to run. Segmentation of heart structures using 3-D computed tomography (CT) may be based on discriminant classifiers and marginal space learning. The segmentation of four heart structures may be achieved in less than eight seconds. However, 3DUS data is different than CT or MRI data. The orientation of anatomical structures in MRI and CT data is generally better constrained than that of 3DUS.

BRIEF SUMMARY

By way of introduction, the preferred embodiments described below include methods, computer readable media and systems for measuring or detecting a fetal parameter from three-dimensional ultrasound data. An algorithm is machine-trained to detect fetal anatomy. Any machine training approach may be used. In one embodiment, the machine-trained classifier is a joint classifier, such that one anatomy is detected using the ultrasound data and the detected location of another anatomy. In one embodiment, the machine-trained classifier uses marginal space such that the location of anatomy is detected sequentially through translation, orientation and scale rather than detecting for all location parameters at once. In one embodiment, the machine-trained classifier includes detectors for detecting from the ultrasound data at different resolutions, such as in a pyramid volume. One or more of the embodiments may be used alone or together.

In a first aspect, a method is provided for measuring a fetal parameter from three-dimensional ultrasound data. A machine-trained classifier is applied to the three-dimensional ultrasound data. A first fetal anatomy is detected as a function of the applying. A value of the fetal parameter associated with the first fetal anatomy is measured and displayed.

In a second aspect, a computer readable storage medium has stored therein data representing instructions executable by a programmed processor for measuring a fetal parameter from three-dimensional ultrasound data. The storage medium includes instructions for receiving user input requesting automatic measurement of a fetal head anatomy, the fetal parameter being for the fetal head anatomy, detecting the fetal head anatomy with a computer learnt classifier, the computer learnt classifier operable to detect from the three-dimensional ultrasound data without user indication of a position, and calculating a value for the fetal parameter.

In a third aspect, a system is provided for measuring a fetal parameter from three-dimensional ultrasound data. A memory is operable to store ultrasound data representing a fetal volume. A processor is operable to apply a probabilistic model to detect a first anatomy as a function of the ultrasound data and a position of a second anatomy. The detection of the first anatomy is performed sequentially for at least two of position, orientation and scale. A display is operable to display an image of the first anatomy, a value representing a measurement of the first anatomy or combinations thereof.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In ultrasound imaging, shadows, speckle noise and other artifacts create a low contrast image with blurry edges. Even if it is easy for the human eye to navigate and recognize structures, it is difficult to adapt common feature extraction techniques to 3DUS datasets. The size of the anatomical structures depends on the age of the fetus, which brings a high variance in the model for each structure. The position and orientation of each fetus is completely arbitrary, making it impossible to constrain the search space in 3D.

A clinical system automatically indexes fetus structures despite the limitations of ultrasound imaging of the fetus for biometric measurements. In one embodiment, a system is based on a machine-trained model. In order to provide a completely automatic solution for the problem of fetal anatomy indexing in 3DUS, a principled probabilistic model combines discriminative and generative classifiers with contextual information and sequential sampling. Contextual information or sequential sampling may be used alone or in combinations. The indexing of fetal anatomies allows the display of standard planes and associated biometric measurements of the fetal anatomy. In response to a user query or other activation, anatomical structures of interest are detected.

Figure 1:
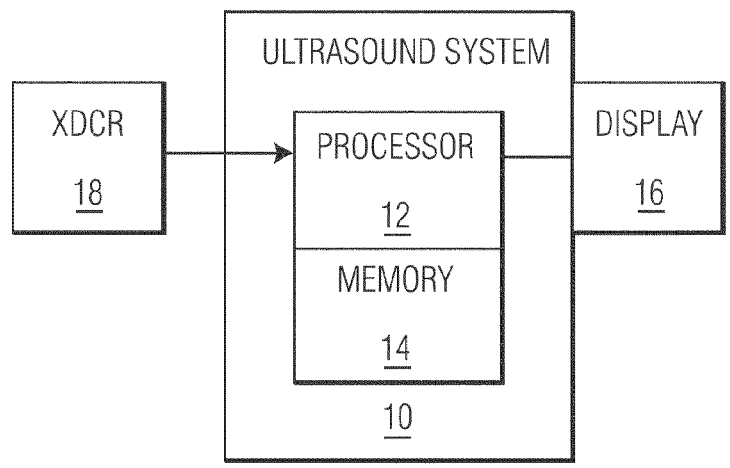
FIG. 1 is a block diagram of one embodiment of a medical ultrasound imaging system.

FIG. 1 shows a medical diagnostic imaging system 10 for measuring a fetal parameter and/or detecting fetal anatomy from three-dimensional ultrasound data. Fetal anatomies may be detected, allowing measurement of the anatomies and reconstruction of standard planes relative to the anatomies from ultrasound volume data.

The system 10 is a medical diagnostic ultrasound imaging system, but may be a computer, workstation, database, server, or other system. The system 10 includes a processor 12, a memory 14, a display 16, and a transducer 18. Additional, different, or fewer components may be provided. For example, the system 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system 10 is a workstation for off-line or later measurement of fetal anatomy.

The transducer 18 is a piezoelectric or capacitive device operable to convert between acoustic and electrical energy. The transducer 18 is an array of elements, such as a multidimensional or two-dimensional array. Alternatively, the transducer 18 is a wobbler for mechanical scanning in one dimension and electrical scanning in another dimension.

The system 10 uses the transducer 18 to scan a volume. Electrical and/or mechanical steering allows transmission and reception along different scan lines in the volume. Any scan pattern may be used. In one embodiment, the transmit beam is wide enough for reception along a plurality of scan lines. In another embodiment, a plane, collimated or diverging transmit waveform is provided for reception along a plurality, large number, or all scan lines.

Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode, Doppler mode, contrast agent, harmonic, or other ultrasound modes of imaging.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a fetal volume. The fetal volume is a volume including at least a portion of the fetal head, but other portions of a fetus may be represented. The memory 14 stores flow (e.g., velocity, energy or both) and/or B-mode ultrasound data. Alternatively, the medical image data is transferred to the processor 12 from another device. The medical image ultrasound data is a three-dimensional data set, or a sequence of such sets. The data represents a three-dimensional region. Any format may be used, such as voxels interpolated to a three-dimensional grid or data representing parallel or non-parallel planes.

For real-time imaging, the ultrasound data bypasses the memory 14, is temporarily stored in the memory 14, or is loaded from the memory 14. Real-time imaging may allow delay of a fraction of seconds, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session used to acquire the data. The amount of delay between acquisition and imaging for real-time operation may vary, such as a greater delay for initially locating fetal anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a computer readable storage medium with processing instructions. The memory 14 stores data representing instructions executable by the programmed processor 12 for detecting fetal anatomy and/or measuring a fetal parameter from three-dimensional ultrasound data. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, detecting anatomy, measuring anatomy, and/or controlling imaging.

In one embodiment, the processor 12 receives acquired ultrasound data during or after scanning and determines locations of one or more fetal anatomies in the volume represented by the data. The processor 12 performs or controls other components to perform the methods described herein.

The processor 12 performs machine learning and/or applies a machine-learnt algorithm. For example, the processor 12 applies a probabilistic model to detect fetal anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. In one embodiment, a binary boosting classifier with a tree and cascade structure is used. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different fetal anatomy. The probabilistic models may be joint or dependent. The location of other anatomies is used to limit or define a search space for a current anatomy and/or as a feature input for classification of another anatomy. For example, one anatomy, such as the fetal head or skull, is detected from the ultrasound data. The position of the anatomy is determined from the volume represented by the ultrasound data. Another anatomy is detected as a function of the ultrasound data and the position of the one anatomy. The other anatomy may be a cerebellum, a cisterna magna, or a lateral ventricle. In one embodiment, the cerebellum is detected based on the location of the fetal skull, the cisterna magna is detected based on the location of the cerebellum and/or the fetal skull, and the lateral ventricle is detected based on the location of the fetal skull, cerebellum, and/or cisterna magna. Other combinations of joint classifiers may be used.

As another example of a plurality of classifiers being used as one, different probabilistic models are trained for translation, orientation, and scale of a given fetal anatomy. A marginal space training and application may provide efficient location detection. The most probable data for a given anatomy by translation searching (shifting the search window along three axes) is determined. The most probable size for a given anatomy by scale searching (increasing and decreasing the size of the search window along three axes) is determined for the translated locations with sufficient probability. The most probable orientation by rotation searching (rotation of the search window along three axes) is determined for the translated and scaled locations with sufficient probability. Other orders of translation, scale, and orientation searching may be used in the sequence. By performing the detection for the anatomy sequentially for at least two of position, orientation and scale, the number of computations may be reduced as compared to classifying for each possible combination of translation, scale, and orientation. In alternative embodiments, translation, scale, and orientation searching are performed without sequentially limiting the search space or without marginal space searching.

In another example of a plurality of classifiers being used as one, different probabilistic models are trained for different data resolutions. A data pyramid is provided, such as the same data set down sampled to different resolutions. Two or more versions of the data may be provided. For example, the ultrasound data has voxels representing about 1×1×1 mm cubes. The data is down sampled by half, providing a data set where each voxel represents a 2×2×2 mm cube. This lower resolution data is down sampled by half, providing a data set where each voxel represents a 4×4×4 mm cube. In alternative embodiments, the voxels have unequal sides or are not isotropic. Different probabilistic models are provided as classifiers for each of the data sets. One classifier is applied to the coarsest set. The results of the course set application are used by the classifier for the next highest resolution, such as by limiting the search space. This repeats until the highest resolution data set is used. In alternative embodiments, a single data set is used.

The different classifiers for joint classification, marginal space classification, and/or multiple resolution classification are the same or different types of classifiers. The same or different types of classifiers may be used for the same type of classification, such as different types of classifiers being used for different marginal space classification (e.g., the classifier for translation is different than the classifier for scale).

In one embodiment, the probabilistic model is formed from a plurality of probabilistic boosting tree classifiers. Separate training and resulting machine-trained classifiers are provided for each anatomy of interest. For each of these separate classifiers, separate probabilistic boosting tree classifiers are provided for each of the marginal space types. For example, the classifiers follow the marginal space learning protocol, providing a position detector using Haar wavelet features, a scale detector using steerable features, and an orientation detector using steerable features. Separate marginal space classifiers are provided for each resolution of data. For example, each detector (e.g., position, scale, and orientation for each anatomy) at 4 mm resolution is a probabilistic boosting tree with 6 levels, and each node in the tree is a strong classifier with at most 20 weak classifiers. Each detector (e.g., position, scale, and orientation for each anatomy) at 2 mm is a probabilistic boosting tree with 8 levels, and each node in the tree is a strong classifier with at most 20 weak classifiers. Each detector (e.g., position, scale, and orientation for each anatomy) at 1 mm is a probabilistic boosting tree with 10 levels, and each node in the tree is a strong classifier with at most 20 weak classifiers. Any number of classifiers, nodes, levels, or other combinations may be used.

The detection algorithm implemented by the processor 12 searches through multiple hypotheses (window locations) to identify the hypotheses with high probabilities for each anatomy. Multiple hypotheses are maintained between algorithm stages. Each stage, such as a translation stage, an orientation stage, and a scale stage, quickly removes false hypotheses remaining from any earlier stages. The correct or remaining hypotheses propagate to the final stage. Only one hypothesis is selected as the final detection result or a measurement location is detected from information for a combination of hypotheses (e.g., average of the remaining hypotheses after the final stage).

For application, the processor 12 calculates features for classification. The same or different features are used for classification in each stage. For example in a translation stage, features are calculated for each of a plurality of translated positions of cubic regions of interest. Using a machine-trained translation classifier, the features are used to rule out hypotheses corresponding to the translated positions, leaving a subset of remaining hypotheses.

The features are three-dimensional features. 3D data is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the "steerable" features described by Zheng, et al. in "Fast Automatic Heart Chamber Segmentation from 3D CT Data Using Marginal Space Learning and Steerable Features," Proc. Int'l Conf. on Computer Vision, pp. 1-8, 2007, are used. Other types of features may alternatively or additionally be used.

Feature values are calculated for each hypothesis. For translation classification at 1 mm for the cerebellum, the features are calculated for each of the possible translated window positions. The same features, such as the same Haar functions, are calculated for each of the possible translated positions. The translation classifier outputs a probability of a given possible position being the correct or desired anatomy based on the feature values. If the probability is above a threshold, the associated hypothesis is maintained. If the probability is below a threshold, the associated hypothesis is ruled out and discarded from the pool of hypotheses.

By ruling out one or more hypotheses, the number of possible positions associated with rotation and/or scale may be limited. For example, ruling out one hypothesis and leaving two hypotheses allows the orientation classifier to calculate features for different rotations relative to two different translations instead of three.

The processor 12 calculates the same or different features for each of a plurality of rotated positions associated with the remaining hypotheses. Hypotheses corresponding to the rotated positions are ruled out with an orientation classifier and as a function of the features. After application of the orientation classifier, a further subset of hypotheses remains. The remaining hypotheses are for sufficient translations having at least one sufficient rotation.

The processor 12 calculates the same or different features for each of a plurality of scaled planes associated with hypotheses remaining after translation and orientation testing. A scale classifier rules out hypotheses corresponding to the scaled windows as a function of the features. After ruling out none, one or more hypotheses, a remaining set of hypotheses remains for the anatomy being detected. Other marginal space orders may be used.

The remaining hypotheses for the lowest resolution data are used for classification using higher resolution data. The marginal space process repeats using the higher resolution data. The process is repeated until one or more hypotheses remain after application of the classifiers for the higher resolution data set. By sequentially ruling out hypotheses for different marginal space and data resolution applications, the number of calculations for detecting a fetal anatomy may be quickly (e.g., seconds) determined using a computer.

The processor 12 calculates measurements of the detected anatomy. Any measurement may be made. In one embodiment, the classifier is trained with measurement annotations, such as caliper positions. The detection of the anatomy provides the caliper positions as an output of the classifier. The measurement corresponding to the caliper position is performed, such as measuring a diameter or distance. Any now known or later developed measurement may be used.

The display 16 is a CRT, LCD, plasma, projector, printer, or other output device for showing an image. The display 16 displays an image of the detected anatomy, such as an image of a standard plane associated with the measurement of the anatomy. The data representing the volume is used for generating the image. Data from the volume dataset adjacent to or intersected by the plane defined by the location of the anatomy is used to generate a cut-plane or planar reconstruction image. The detected anatomy may or may not be highlighted or segmented. Alternatively or additionally, a value of the measurement is displayed. The value may be displayed in a chart, graph, and/or on an image.

Figure 2:
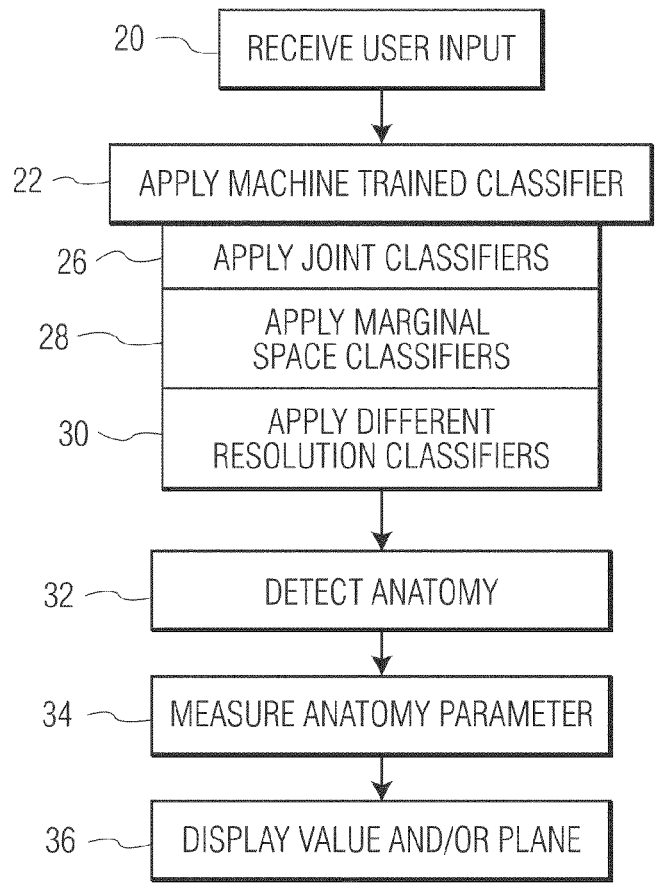
FIG. 2 is a flow chart diagram of embodiments of a method for measuring a fetal parameter from three-dimensional ultrasound data.

FIG. 2 shows a method for measuring a fetal parameter and/or detecting fetal anatomy from three-dimensional ultrasound data. The method is implemented by a medical diagnostic imaging system, a review station, a workstation, a computer, a PACS station, a server, combinations thereof, or other device for image processing medical ultrasound data. For example, the system or computer readable media shown in FIG. 1 implements the method, but other systems may be used.

The method is implemented in the order shown or a different order. Additional, different, or fewer acts may be performed. For example, act 36 is optional. As another example, one or more of acts 26, 28, and 30 are not performed.

The acts are performed in real-time, such as during scanning. The user may view images of act 36 while scanning to acquire another dataset representing the volume. The images may be associated with previous performance of acts 20-36 in the same imaging session, but with different volume data. For example, acts 20-36 are performed for an initial scan and for subsequent scans during the same imaging session. Measurements and/or images of automatically detected anatomy may be provided in seconds, such as 10 or fewer seconds.

For training and/or application, ultrasound data representing a volume containing the head of a fetus between 13 to 35 weeks of age is used. After 35 weeks, the ultrasound signal has difficulty penetrating the fetal skull. Alternatively, the volume represents the entire fetus or only other portions of the fetus.

One or more sets of data are obtained. The ultrasound data corresponds to a data set interpolated to a regular 3D grid, displayed images (e.g., detected and scan converted ultrasound data), beamformed data, detected data, and/or scan converted data. The ultrasound data represents a volume or 3D region of a patient. The region includes tissue, fluid or other structures. Different structures or types of structures react to the acoustic energy differently. The shape of a structure or spatial aspect may be reflected in B-mode or harmonic data. The fetal head or other portion of the fetus is within the volume region. The data represents the region.

In act 20, user input is received. The user input requests automatic measurement or detection of fetal anatomy, such as fetal head anatomy. The measurement is a parameter associated with the fetal head anatomy. For example, measurement of the diameter of the cerebellum is requested. In alternative embodiments, the measurement and/or detection occur without user request, such as in response to activation of a three-dimensional fetal imaging application.

The user input is data, an electrical signal, or other information useable by a processor to indicate user activation. For example, the electrical signal generated in response to user depression of a button or other user interface selection (e.g., pointer-based selection) indicates a user request. The context of the information shows the aspect requested (e.g., request of all available automatic fetal head measurements based on user selection of a menu item for such request).

In one semantic embodiment, the user input is text. A semantic keyword is input as a user query. The user may query the system using a limited vocabulary of semantic keywords. Each keyword represents an anatomy of interest that the user wants to visualize and/or measure. For example, cerebellum, cisterna magna, and lateral ventricles anatomies may be detected and measured. Once the user selects the keyword, the system automatically shows the standard plane of visualization and/or the respective biometric measure by implementing acts 22-36.

In act 22, a machine-trained classifier is applied to the three-dimensional ultrasound data. The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perception), mixture models, or others. A probabilistic boosting tree may be used. Error-correcting output code (ECOC) may be used.

The classifier is trained from a training data set using a computer. Any number of expert annotated sets of ultrasound data is used. For example, about 200 hundred ultrasound volumes representing fetal heads and including the cerebellum, cisterna magna and lateral ventricles are annotated. The annotation is a line, points, curves or volumes associated with a measurement of the respective anatomy. The different anatomies of each volume are annotated. This large number of annotations allows use of a probabilistic boosting tree to learn relevant features over a large pool of 3-D Haar features and steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies and/or measurement indicators for the anatomies. Training and detecting the location of measurement indicators include detecting the associated anatomy since the measurement indicator (e.g., a line representing the diameter) indicates the anatomy. The known cases may be spatially aligned or registered, such as by aligning the coordinate system to the fetal skull. The detectors are trained on a large number of annotated 3D ultrasound volumes. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

A tree structure may be learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. For example, the translation, orientation, and scale classifiers are trained as a probabilistic boosting tree. A probabilistic boosting tree is learned for each anatomy of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques, such as disclosed by Tu, "Probabilistic Boosting-Tree: Learning Discriminative Models for Classification, Recognition, and Clustering," Proc. Int'l Conf. on Computer Vision, pp 1589-1596, 2005.

The classifier is trained and applied as a machine-trained joint, marginal space, and/or different resolution classifier. Any combination of one or more of joint classification (act 26), marginal space classification (act 28), and different resolution classification (act 30) may be used. The resulting machine-trained classifier is applied as a detector of the cerebellum, fetal cisterna magna, fetal lateral ventricles, or combinations thereof. The classifier may be trained to detect different, additional, or fewer fetal anatomies.

In act 26, a joint classifier is applied. The joint classifier includes different classifiers for different fetal anatomies. For joint classification, at least one of the anatomies is detected as a function of the previous detection of another of the anatomies. For example, a machine-trained head detector detects the location of a center of a fetal skull in a desired plane. Another machine-trained detector detects the location of the cerebellum, cisterna magna, lateral ventricles, combinations thereof, or other anatomy from the ultrasound data and as a function of the location of the center of the fetal skull. Some of the machine-trained detectors have an input for the location detected from one or more other detectors of different anatomy, so are dependent on the output of the other machine-trained head detectors.

Joint classification uses contextual information. In one embodiment, the contextual information is based on one or two cues: 1) global context based on the detection of the fetal skull, and 2) semi-local context based on the relative position, orientation and scale between anatomies. These cues may be modeled with generative classifiers. The fetal skull is the largest and most visible structure in 3D ultrasound. Thus, the fetal skull may be more reliably used as a reference to constrain the search space of other anatomies in the fetal brain.

Figure 3:
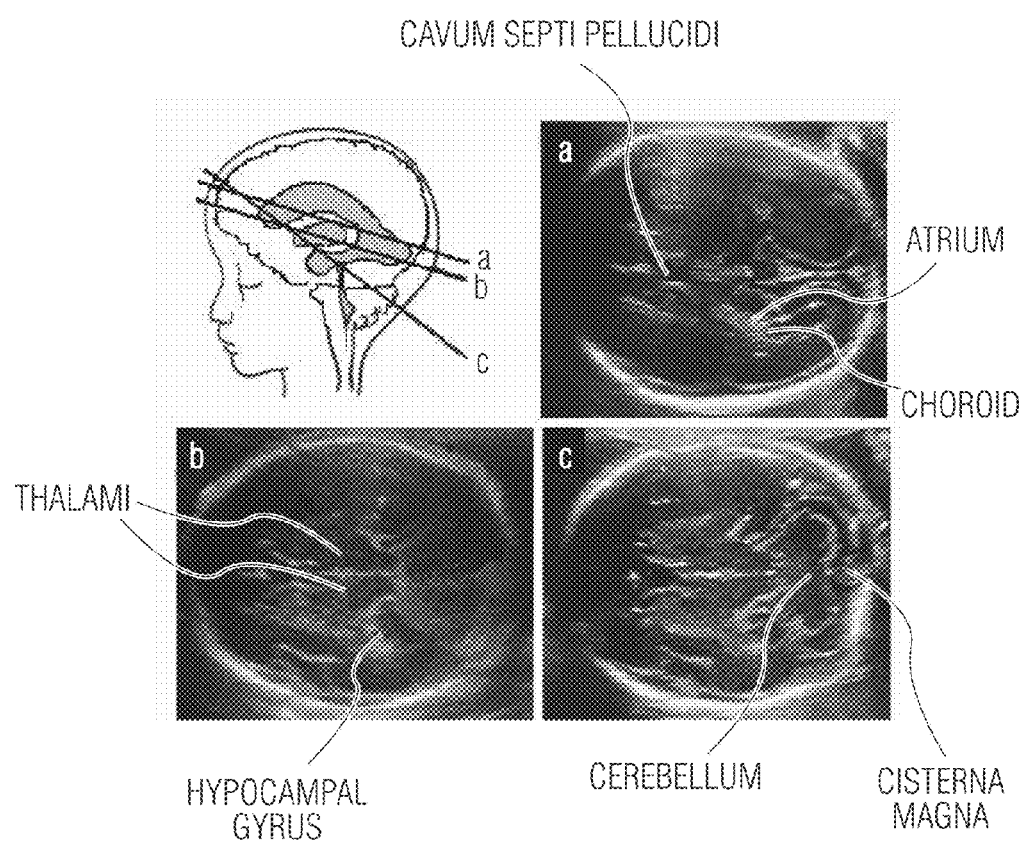
FIG. 3 is a graphical representation of planes in a fetal head and corresponding reconstruction images in one embodiment.

A volume is a 3-D mapping V: $R^3 \rightarrow [0, 255]$. A sub-volume window containing a particular anatomical structure is represented by a vector containing position, size and orientation, as follows:

$$\theta_s = [p, \sigma, q] \in R^7, \quad (1)$$

where $p=[x, y, z] \in R^3$ is the three dimensional center of the sub-volume, $\sigma \in R$ represents its size, $q=[q_1, q_2, q_3] \in R^3$ represents orientation (e.g., represented using quaternions) and s represents a specific anatomy (here, $s \in \{$CB (center brain), CER (cerebellum), CM (cisterna magna), LV (lateral ventricles)$\}$. FIG. 3 shows example planes and anatomies. The sub-volume parameters of all the anatomies of interest:

$$[\theta^*_{CER}, \theta^*_{CM}, \theta^*_{LV}] = \underset{\theta_{CER}, \theta_{CM}, \theta_{LV}}{\mathrm{argmax}} \; P(\theta_{CER}, \theta_{CM}, \theta_{LV} \mid V) \quad (2)$$

are determined, where $P(\theta_{CER}, \theta_{CM}, \theta_{LV}|V)$ indicates a probability measure of the anatomy parameters given the volume V. The search space for this case is $O((M^7)^L)=O(M^{21})$, where each dimension is assumed to be partitioned into M values, and L=3 is the number of anatomies to detect. An example value for M is in the order of 100.

The context may be used to prune the search space, possibly improving the accuracy and increasing the speed of the recognition systems. Any type of context may be used. For example, global and semi-local contexts are used.

The global context is provided by the center of the brain (CB) structures derived from the whole skull of the fetus. CB may be the largest and most distinctive feature in a 3D fetal ultrasound, so may be found reliably in most datasets. As context, the CB may be used to constrain the search space for the other anatomies. Thus, equation (2) can be denoted as:

$$[\theta^*_{CER}, \theta^*_{CM}, \theta^*_{LV}] = \underset{\theta_{CER}, \theta_{CM}, \theta_{LV}}{\mathrm{argmax}} \int_{\theta_{CB}} P(\theta_{CB}, \theta_{CER}, \theta_{CM}, \theta_{LV} \mid V) d\theta_{CB}. \quad (3)$$

Assuming the existence of the random variable $y_s = \{-1, 1\}$ for $s \in \{$CB, CER, CM, LV$\}$, where $y_s = 1$ indicates the presence of the anatomy s, the result is:

$$P(\theta_{CB}, \theta_{CER}, \theta_{CM}, \theta_{LV}|V) = P(\{y_s=1\}_{s \in \{CB, CER, CM, LV\}} | \theta_{CB}, \theta_{CER}, \theta_{CM}, \theta_{LV}, V). \quad (4)$$

Discriminative classifiers capable of computing actual posterior probabilities (e.g., PBT) may be trained and applied for each anatomy. The following or other probabilities may be computed: $P(y_s=1|\theta_s, V)$ for $s \in \{$CB,CER,CM,LV$\}$ (hereafter $P(y_s=1|\theta_s, V) = P(y_s|\theta_s, V)$). Using the Bayes rule, equation (4) is derived to:

$$P(y_{LV}|y_{CB}, y_{CER}, y_{CM}, \theta_{CB}, \theta_{CER}, \theta_{CM}, \theta_{LV}, V),$$

$$P(y_{CB}, y_{CER}, y_{CM}|\theta_{CB}, \theta_{CER}, \theta_{CM}, \theta_{LV}, V)$$

which can be further derived to:

$$\frac{P(y_{LV} | \theta_{LV}, V) \cdot P(y_{CB}, y_{CER}, y_{CM} | \theta_{CB}, \theta_{CER}, \theta_{CM}, V) \cdot P(\theta_{LV} | y_{CB}, y_{CER}, y_{CM}, \theta_{CB}, \theta_{CER}, \theta_{CM}, V)}{P(\theta_{LV} | \theta_{CB}, \theta_{CER}, \theta_{CM}, V)}.$$

The probability of the presence of LV based on the feature values is assumed to depend only on $\theta_{LV}$ and V, but the probability distribution of $\theta_{LV}$ depends on the detection and parameters of other anatomies. This is an assumption of parts independence but geometry dependency. The conditional distribution of $\theta_{LV}$ given all other parameters is assumed to be a uniform distribution because there is no notion about the actual presence of the other anatomies. Finally, equation (4) may be written as follows:

$$P(\theta_{CB}, \theta_{CER}, \theta_{CM}, \theta_{LV} | V) = \quad (5)$$

$$P(y_{LV}|\theta_{LV}, V) P(y_{CM}|\theta_{CM}, V) P(y_{CER}|\theta_{CER}, V) P(y_{CB}|\theta_{CB}, V)$$

$$P(\theta_{CER}|y_{CB}, \theta_{CB}, V) \cdot P(\theta_{CM}|y_{CB}, y_{CER}, \theta_{CB}, \theta_{CER}, V)$$

$$P(\theta_{LV}|y_{CB}, y_{CER}, y_{CM}, \theta_{CB}, \theta_{CER}, \theta_{CM}, V),$$

where the first four terms are the posterior probabilities of each anatomy, and the remaining terms account for the global and semi-local context. The detection probability described in equation (5) suggests a sequential detection where CB is detected first, followed by CER, then CM, and finally LV. Other orders may be used. Using context, the complexity of the detection may be reduced from $O(M^{7L})$ in its original form of equation (2) to $O(L+1) \times M^7$.

Additionally or alternatively, semi-local context may constrain even more the search space of the sought anatomy given the anatomies already found. For semi-local context, during the detection process, the parameter values of the detected anatomies are used to estimate a distribution in the parameter space for the subsequent anatomies to be detected. For position, scale, and orientation parameters, it is possible to determine an orthonormal matrix $R_s \in R^{3 \times 3}$ with the three axis of the coordinate system lying in its rows using the orientation parameters. To produce scale invariant estimates of position for anatomy j given the parameters of anatomy i (i.e., $\theta_i$):

$$P_{j|i} = R_i\left(\frac{P_j - P_i}{\sigma_j}\right), \quad (6)$$

where $P_s \in R^3$ and $\sigma_s \in R$ are the center and scale of anatomy s, respectively. Given a training set $\{\theta_s(k)\}_{k=1,\ldots,N}$, where k is an index to a training sample, a least squares optimization is formulated for the scale invariant conditional position as:

$$\mu_{p(j|i)} = \underset{P_{j|i}}{\mathrm{argmin}} J(P_{j|i}), \quad (7)$$

where:

$$J(P_{j|i}) = \frac{1}{2}\sum_k (P_j(k) - \sigma_j(k) R_i^T(k) P_{j|i})^2, \quad (8)$$

reading to:

$$\mu_{p(j|i)} = \frac{1}{N}\sum_k R_{i(k)}\left(\frac{P_j(k) - P_i(k)}{\sigma_j(k)}\right) \quad (9)$$

Assuming a Gaussian distribution for $p_{j|i}$, the position covariance may be computed as:

$$\sum_{p(j|i)=} \frac{1}{N}\sum_k (P_{j|i}(k) - \mu_{p(j|i)})(P_{j|i}(k) - \mu_{p(j|i)})^T. \quad (10)$$

The estimation of the scale of anatomy i given the scale of anatomy j is denoted as $$\sigma_{j|i} = \frac{\sigma_j}{\sigma_i}. \quad (11)$$

Again, considering a Gaussian distribution for $\sigma_j|_i$:

$$\mu_{\sigma(j|i)} = \frac{1}{N}\sum_k \frac{\sigma_j(k)}{\sigma_i(k)} \quad (12)$$

$$\sum_{\sigma(j|i)} = \frac{1}{N}\sum_k (\sigma(j|i) - \mu\sigma(j|i))^2.$$

Finally, the estimation of the orientation of anatomy i given the orientation of anatomy j is denoted as $$q_{j|i} = q_i + d_q(q_j, q_i), \quad (13)$$

where $d_q(.)$ is a function that computes difference between quaternions. Considering a Gaussian distribution for $q_{j|i}$:

$$\mu_{q(j|i)} = \frac{1}{N}\sum_k d_q(q_j(k) - q_i(k)) \quad (14)$$

$$\sum_{q(j|i)=} \frac{1}{N}\sum_k (q(j|i) - \mu_{q(j|i)})(q(j|i) - \mu_{q(j|i)})^T$$

Given the parameter estimations above, the computation of the semi-local context probabilities are as follows:

$$P(\theta_j \mid \{y_l = 1, \theta_l\}_{l=1,\ldots,L}, V) = g\left(\left[\frac{1}{L}\sum_l R_l \frac{P_j - P_l}{\sigma_l}, \frac{1}{L}\sum_l \sigma_j/\sigma_l, \frac{1}{L}\sum_l d_q(q_j, q_l)\right]; [\mu_{p(j|\{l\})} \mu_{\sigma(j|\{l\})} \mu_{q(j|\{l\})}], \sum\right) \quad (15)$$

with:

$$\sum = \begin{bmatrix} \sum_{p(j|\{l\})} & 0 & 0 \\ 0 & \sum_{\sigma(j|\{l\})} & 0 \\ 0 & 0 & \sum_{q(j|\{l\})} \end{bmatrix}$$

and:

$$g(x; \mu, \sum) = \frac{1}{(2\pi)^{7/2}|\Sigma|^{1/2}} \exp = \frac{1}{2}(x-\mu)^T \sum{}^{-1}(x-\mu)),$$

where $\theta_j = [p_j, \sigma_j, q_j]$ is the parameter for anatomy j, l is an index to the previous L detections, and $[\mu_{p(j|\{l\})} \mu_{\sigma(j|\{l\})} \mu_{q(j|\{l\})}]$ is computed by taking the sample average of the estimations, and similarly for $\Sigma$.

With the use of semi-local context, the complexity of the detection algorithm is unaltered. In practice, only places where the semi-local context probability is above a threshold are searched. Empirically, places in the parameter space that are further than 2 times the covariance of the estimated Gaussian may be avoided or not searched. In general, this reduces the search space at each search parameter dimension from M to M ½ (in embodiment, M≈100). As a result, in practice the complexity of the detection is reduced from $O(M^{7L})$ in its original form of equation (2) to $O(M^7 + L \times M^{2^7})$. Consequently, the use of semi-local and global context information makes this approach linearly scalable in terms of the number of brain anatomies.

In act 28, the classifier is applied as a sequence of marginal machine-trained classifiers to the three-dimensional ultrasound data. One marginal machine-trained classifier is for translation of a given fetal anatomy within a volume represented by the three-dimensional ultrasound data. Another marginal machine-trained classifier is for rotation of the given fetal anatomy within the volume. Yet another marginal machine-trained classifier is for scale of the given fetal anatomy within the volume.

The pose estimation for each fetal anatomy may involves 3-D position, orientation and scale resulting in 7 or 9 degrees of freedom (i.e., a total of 21 or 27 degrees of freedom for all anatomies) in a typical volume of dimensions 250×200×150 voxels. This large dimensional search space makes a brute force approach not practical. Thus, to make the problem tractable, sequential sampling and contextual information are used.

A sequence of machine-trained classifiers is learned and/or applied to the three-dimensional ultrasound data. Anatomy detection estimates the pose parameters (i.e., position) for each anatomy. The pose parameters of a 3D rigid body may include 9 components: 3 translations (x, y; z), 3 orientations (e.g., Euler angles w.r.t. for each axis), and 3 scales (one for each axis). One or more of the parameters may not be used, such as not providing scale or only providing scale along one axis or the same for all three axes.

Searching in a high-resolution 3D volume is prohibitive for online applications or rapid determination. For example, a volume of 100×100×100 voxels has $10^6$ hypotheses for translation. If combining orientation and scale, a combinatorial hypothesis search space expands dramatically. A limited set of hypotheses may be used based on any desired criteria, such as relative expected positions of different anatomy. By training a series of detectors that estimate anatomy pose parameters at a number of sequential stages, the number of calculations may be reduced. The stages are applied in the order of complexity as the parameter degrees of freedom increase (e.g., translation, then orientation, and then scale), but other orders may be used. For example, scale may be adjusted only along two axes given a translation and orientation. In other embodiments, other learning with or without hierarchical searching is used.

Sequential sampling is used to model probability distributions. The posterior classifiers are modeled to compute $P(y_s|\theta_s, V)$. Sequential sampling or marginal space learning provides efficient training and detection approaches for high-dimensional search parameter spaces. The original parameter space $\Omega$ is broken into subsets of increasing dimensionality $\Omega_1 \subset \Omega_2 \subset \ldots \subset \Omega$, and then classifiers are trained for each subset. The samples for training the classifier in $\Omega_n$ are bootstrapped from $\Omega_{n-1}$, and the classifier in $\Omega_1$ is trained using all possible samples.

In one embodiment, the following sequence is assumed: $\Omega_1 = p \in R^3$, $\Omega_2 = [p_s, \sigma_s] \in R^4$, and $\Omega_3 = \Omega = [p_s, \sigma_s q_s] \in R^7$. The actual search space for training and detection in $\Omega_n$ is defined to be $\dim(\Omega_n) - \dim(\Omega_{n-1})$, where $\dim(\Omega_n)$ denotes the dimensionality of the $Q_n$ space. In each subspace, a discriminative classifier is trained using the PBT algorithm (i.e., forming $PBT_n$ for each $\Omega_n$) due to its ability of representing multimodality distributions in binary classification problems.

This process results in a training and detection complexity figures of $O(M^3)$, where M is the number of quantized parameter values per dimension. This represents a reduction in terms of complexity of the original algorithm in equation (2). Sequential sampling and the use of contextual information reduce the complexity from $O(M^{7L})$ to $O(M^3 + L \times M^{3/2})$. This reduction allows for the detection of additional anatomies with little impact on the overall detection complexity.

Orientation may be determined using quaternions or Euler angles. The space of possible orientations is usually represented with the three Euler angles. Euler angles are easy to implement and understand, but they have several drawbacks to represent the orientation space. First, a uniform step size over possible Euler angles does not generate a uniform sampling in the space of orientations, which makes Euler angles impractical for uniform sampling. Second, the representation for each orientation is not unique, which makes it difficult to define a similarity measure between two orientations expressed in Euler angles. In other words, Euler angles are a chart of the space of orientations with singularities (i.e., non-smooth). Consequently, two similar orientations might have very different Euler angles, which make it difficult to compute statistics and distances. For example, if the Z×Z-convention is selected with $(\gamma, \beta, \alpha)$ as the three Euler angles, a singularity is provided along the line $\beta=0$. The triplet (0.7, 0.0, 0.3) gives the same orientation as the triplet (0.0, 0.0, 1.0).

The concepts on quaternions proposed for molecular modeling may be used to represent the space of orientations in 3D. The problems above are solved using unitary quaternions to express orientations. Each orientation may be defined as a point in the hypersphere $S^3 = 3\{p \in R^4 | \|p\|_2 = 1\}$ with opposite points identified. This equivalence relation defines the space of orientations as the following quotient space:

$$SO(3) = S^3/\{q, -q\} | q = [q_1, q_2, q_3, q_4] \in R^4; \|q\|_2^2 = 1\},$$

where the operator "/" denotes the quotient space given by the identification of $\{q \sim -q\}$ in $S^3$. Two properties from quaternions are used. First, composition of two rotations may be computed as a multiplication of two quaternions. If R(q) with $q \in SO(3)$ represents one orientation and R(p) with $p \in SO(3)$ represents another, then $R(p) \circ R(q) = p \cdot \bar{q}$ where $\bar{q}$ is the conjugate of $q^1$. Second, there is a distance preserving map between SO(3) and a ball in $R^3$. This map allows use in SO(3) of standard statistical tools from $R^3$.

[1] $\bar{q} = [q_1, -q_2, -q_3, -q_4]$

Each quaternion may also be expressed as $q = [\cos(\theta/2) v \cdot \sin(\theta/2)] \in SO(3)$ with $v \in R^3$ s.t. $\|v\|_2 = 1$ and $\theta \in (-\pi, \pi)$. v represents the axis of rotation and $\theta$ the angle of rotation around that axis. Then, the definition of the distance preserving map is the following:

$$f: SO(3) \to \qquad (16)$$

$$q \mapsto u \text{ with } u\|v \text{ and } \|u\| = \left(\frac{|\theta| - \sin(|\theta|)}{II}\right)^{\frac{1}{3}}$$

The same way a hemisphere may be "flattened" into a disc in $R^2$ preserving geodesic distances, Equation (16) "flattens" the quotient space into a ball in $R^3$.

Using the two properties explained above, the orientations may be manipulated, and statistics and metrics may be computed in the space of orientations. $d_q(q_j, q_i)$ in equation (13) may be defined as:

$$dq(q_j, q_i) = \|f(q_j) - f(q_i)\|_2, \qquad (17)$$

where f is defined in equation (16).

The space of orientations may be sampled uniformly with different angle precision. The sampling points for different resolutions may be stored in memory since the sampling points are not easy to calculate on the fly. For example, to achieve 110 accuracy, only 7416 samples are needed. Using constant step size in Euler angles 36*36*18=23328 samples are needed. Since the complete space of orientations in 3DUS is sampled, quaternions bring calculation savings to this task.

The orientation is determined as part of the marginal space approach. The classifiers for this sequential approach are the same or different. For example, different features are used for translation, orientation, and/or scale. For the classifiers at the translation stage, Haar wavelet-like features are used, but other features may be provided. Haar wavelet-like features are calculated efficiently using integral image-based techniques. For classifiers at the rotation and scale stages, gradient or steerable features are used, but other features may be provided. Steerable features constitute a flexible framework, where a few points are sampled from the volume under a spatial pattern (e.g., a regular grid). A few local features are extracted for each sampling point, such as voxel intensity and gradient. To evaluate the steerable features under a specified orientation, the sampling pattern is controlled, and no computationally expensive volume rotation is involved. The computation of steerable features does not require volume rotation and re-scaling, which are computationally expensive.

To apply the classifier, features are calculated. The features are calculated for each of the possible anatomy positions. Other features may be calculated regardless of the possible anatomy position, such as where a feature for a sub-volume may be determinative in combination with other features.

For each possible anatomy position, the features for a given classification are calculated. For the translation stage, the possible anatomy positions relate to different positions translated along three axes. For example, Haar features are calculated for classifying whether a given translation possible anatomy position may be the desired anatomy. For the rotation stage, the possible anatomy positions relate to rotation about the three axes at remaining translation positions. For the scale stage, the possible anatomy positions relate to different size regions at the remaining rotation and translation positions. Different features may be calculated for different stages. Different features may be calculated for different views being detected.

In act 30, the classifier is trained and applied to the ultrasound data at different resolutions. For example, one detector is applied to a coarse sampling of the ultrasound data. Another detector is applied to a finer sampling of the ultrasound data. The search space of the later applied detector is a function of an output of the earlier applied detector. For example, the course sampling is used to determine a location, and the search for applying a detector to a finer sampling is centered around the location. More than two different samplings and associated detectors may be used, such as providing three or more different resolutions of data. Any order of coarse-to-fine, fine-to-coarse, or other orders may be used for sequential sampling.

For sequential sampling to provide data at different resolutions, the initial parameter space is partitioned into subspaces of increasing dimensionality, where the PBT classifiers are trained sequentially in each of these sub-spaces using bootstrap samples. A pyramid data structure is provided. The training sets are selected for the detectors at different levels depending on the complexity of the detection task. At the coarse level, the negative anatomy positions are far from the positive anatomy positions and randomly sampled across reasonable configurations while maintaining a relatively large gap (e.g., any empirically determined spacing) from the positives. At the fine level, negatives are selected only within an empirically determined neighborhood of the positives in accordance with the search strategy, while decreasing the gap in between as compared to the coarse level.

The same pyramid sequence is used during the detection process. The features are calculated from the ultrasound data representing the volume. The features are calculated from the data at different resolutions. The sets represent the same object in the same volume. Features are calculated from a coarse set and then in a fine set of the volume pyramid. The machine learning may determine the determinative features. For each determinative feature, a data set at the corresponding resolution is provided.

The classification using data at different resolutions is used alone or in combination with joint and/or marginal space application. For example, the translation, orientation, and scale for detecting the cerebellum is performed sequentially using coarse data (e.g., the original data set down sampled by 4, such as 1 mm voxels down sampled to represent 4 mm). The translation, orientation, and scale for detecting the cerebellum are performed sequentially again using data at a mid-range of sampling (e.g., the original data set down sampled by 2, such as 1 mm voxels down sampled to represent 2 mm). The translation, orientation, and scale for detecting the cerebellum are performed sequentially again using data at the highest resolution data (e.g., the original data set, such as 1 mm voxels). The output from the last detector or classifier is one or more hypotheses for the location of the cerebellum or cerebellum measurement. This output is used as an input for locating the cisterna magna. The detection of the cisterna magna uses the different resolution data and marginal space detection, similar to the detection for the cerebellum, but limited or assisted by the cerebellum location.

In act 32, a fetal anatomy is detected as a function of the applying. By applying the machine-trained classifier, an anatomy is detected. The anatomy may be detected in whole or in part, such as detecting the location of a point, line, or volume corresponding to the anatomy. For example, the fetal head is detected with a computer-learnt classifier. The detectors determine if a given sub-volume sample (data for a possible anatomy position) is positive or negative.

The detection may be performed in response to user activation, but is performed without user assistance. For example, the computer-learnt classifier detects the anatomy from the three-dimensional ultrasound data without user indication of a position. In alternative embodiments, the user confirms, adjusts, or assists in the detection.

Any fetal anatomy may be detected. For example, the fetal head, cerebellum, cisterna magna, and lateral ventricles are detected.

Each anatomy is detected independently or dependently on other detection. Each anatomy is detected using any number of degrees of freedom of the search window, such as translation, orientation, and scale alone each of three axes. The location searching is performed simultaneously or sequentially. One or more sets of data representing the same volume may be used, such as using a pyramid data structure. In one embodiment, a joint, hierarchal, marginal space classifier is used. One or more anatomies are located, in part, based on the location of another anatomy. Each anatomy is located using data at different resolutions sequentially and with marginal space sequential searching.

For joint detection, the computer learnt classifier is a joint classifier. The joint classifier detects a fetal head anatomy as a function of a location of other anatomy. For example, a fetal head is detected with a first probabilistic boosting tree classifier. The cerebellum, cisterna magna, lateral ventricle or combinations thereof are detected using other probabilistic boosting tree classifiers with the probability distribution and/or search space limited based on the detected fetal head and/or other anatomies.

For marginal space classification, the computer learnt classifier is a marginal space classifier. A translation detector searches for translation. A scale search by a scale detector is limited by a position output by translation detector. An orientation search by an orientation detector is limited by a scale output by the scale detector and/or the position output by the translation detector. This sequential detection may limit complexity or increase efficiency. Possible anatomy positions are ruled out by sequentially calculating the features for translated possible positions, for scaled possible positions, and for rotated possible positions. Each stage removes possible positions from a hypotheses list.

Any step size or search strategy may be used, such as a coarse search with a fine search at the locations identified as likely in the coarse search. The detector provides a probability for each possible position. The possible positions associated with sufficient probability are maintained in the hypotheses pool. Sufficient probability is determined by a threshold, by selecting the top X (where X is one or more) probabilities, or other test. The spatial distributions of probabilities may be used to adjust the search, further reducing calculations.

The detectors are trained for different resolutions of the ultrasound data in a volume pyramid. Different detectors sequentially detect using ultrasound data at different resolutions.

The detected anatomy is the possible position with the highest probability output by the classifier. Alternatively, the detected anatomy is the possible position with the highest average probability from the marginal space and/or data resolution stages. In other embodiments, an average position of the remaining sufficient possible positions is determined. The average position is the detected anatomy. Other limitations may be used, such as averaging the position of the top Y most possible positions. Alternatively, the average measurement is used.

In act 34, a value of the fetal parameter associated with the fetal anatomy is measured. The value is calculated from the ultrasound data associated with the anatomy and/or from spatial or temporal locations associated with the anatomy. Any parameter may be calculated, such as distance, circumference, volume, change, velocity, acceleration, or other anatomy parameter. For example, a line representing the fetal anatomy is determined. The line may be a longest diameter for the anatomy in a given view. In one embodiment, the machine-trained classifier outputs the line. The annotated data used for training is annotated with the measurement line so that the output is the spatial line to be measured. Using the voxel size, the distance associated with the line is calculated. The parameters are specific to a doctor, practice, or hospital. Alternatively, the biometric measurements of the anatomies are performed according to guidelines, such as the guidelines of the International Society of Ultrasound in Obstetrics and Gynecology.

In act 36, the calculated value and/or an image are displayed. The value is displayed as text, in a chart, or as part of a table. The value may be labeled, such as indicating the parameter represented by the value and the units of measurement. Other information may be displayed, such as the gestational age derived from the value.

For an image, a planar reconstruction is created from the three-dimensional ultrasound data. The anatomy may have a standard or predetermined view associated with the measurement. For example, the plane includes the line used for measurement. Ultrasound data corresponding to the view is extracted from the volume. The data is used to generate an image for the view. Data associated with locations intersecting each plane or adjacent to each plane is used to generate a two-dimensional image. Data may be interpolated to provide spatial alignment to the view, or a nearest neighbor selection may be used.

Images are generated for each of the anatomies. One view may be used for multiple anatomies. All or a sub-set of the specific views are generated. The images may be highlighted and/or annotated to indicate the anatomy or the measurement locations. Fewer than all available views may be provided, such as displaying no more than three views and having a priority list of views.

One example of training and application discussed for FIG. 2 is provided. 240 volumes with expert annotations of cerebellum, cisterna magna, and lateral ventricles are collected. Other anatomies and/or numbers of volumes may be used. The annotations are the measurement lines for each feature. The volumes have an average size of 250×200×150, but other sizes may be used. The annotation for the center of the brain uses the same annotation plane as the Cerebellum. This annotation is a line through the midline of the brain, but other planes or annotations may be used. The training volumes for each anatomy are obtained by building a cubic sub-volume around the annotation of size k times bigger the annotation length (e.g., k=2 for CER, k=7 for CM, k=5 LV, and k=1.5 for CB). Other sub-volumes may be used.

The $PBT_1$, or marginal classifier for position, is trained with positive samples formed by a box around the center location of the annotated anatomy with fixed size and oriented according to the volume orientation (i.e., not according to the annotation orientation). The negative samples are formed with boxes from positions $\delta_p$ away from this center (e.g., $\delta_p$=3 voxels). The features used for $PBT_1$ are the 3-D Haar features because of the high efficiency in computation using integral volumes. The classifier for position and scale, $PBT_2$, is trained with positive samples formed by a box around the center of the anatomy with size proportional to the length of annotation, but oriented according to the volume orientation. The negative samples are boxes $\delta_p$ away from the center and $\delta_s$ away in terms of scale (e.g., $\delta_s$=2). Finally, for $PBT_3$, or the orientation classifier, the positive training samples have boxes located at the anatomy center, proportional to scale and at the correct orientation. Negative samples are boxes $\delta p$, $\delta_s$, and $\delta_q$ away (e.g., $\delta_q$=0.2). For $PBT_{2,3}$, steerable features are used because of the efficiency of their computation. The main advantage is that, differently of the 3-D Haar features, it is not necessary to perform volume rotations to compute steerable features. The training of $PBT_n$ uses bootstrapped samples from $PBT_{n-1}$. The process explained above produces the discriminative classifier $P(y_s=1|\theta_s, V)$. The semi-local context parameters are learned generatively.

200 volumes are used for training and 40 volumes are used for testing. The training and test volumes are randomly selected, and there is no overlap between the training and test sets. The results produced by the automated system are compared with the results from an inter-user variability experiment conducted with two OBGYN experts who measured the Cerebellum, Cisterna Magna, and Lateral Ventricles on the same volumes. The average and standard deviation of the inter-user variability and system error for position, scale, and orientation are respectively computed as follows:

$$\mu_p = \frac{1}{N}\sum_{i=1}^{N}\|p1_i - p2_i\|, \quad \sigma_p^2 = \frac{1}{N}\sum_{i=1}^{N}(\|p1_i - p2_i\| - \mu_p)^2, \quad (18)$$

$$\mu_\sigma = \frac{1}{N}\sum_{i=1}^{N}|\sigma1_i - \sigma2_i|, \quad \sigma_\sigma^2 = \frac{1}{N}\sum_{i=1}^{N}(|\sigma1_i - \sigma2_i| - \mu_\sigma)^2,$$

$$\mu_q = \frac{1}{N}\sum_{i=1}^{N}|d_q(q1_i - q2_i)|, \quad \sigma_q^2 = \frac{1}{N}\sum_{i=1}^{N}\|d_q(q1_i - q2_i)| - \mu_p)^2$$

where N is the number of volumes for testing and $d_q(.,.)$ is defined in equation (17). The annotations of one expert are assumed to be the ground truth results. In equation (18), the index 1 denotes ground truth (i.e., one of the users) while 2 indicates either the measurements by the other user for the case of the inter-user variability or the system automatic measurements for the computation of the system error. The average error of the automatic results produced by the system is within the range of inter-user variability for all cases except for 10% to 20% of the cases for Cerebellum and Cisterna Magna position. Empirically, one tradeoff between robustness to imaging variations, noise, and pose variance and accuracy is achieved by running the system on a pyramid of volumes where the coarse scale is 4 mm/voxel (isotropic) and the finest scale is 2 mm/voxel. Consequently, the error results produced by the system have a different scale than the inter-user variability that partially explains this discrepancy.

This fully automatic approach may performs quickly (e.g., under 10 seconds in a dual-core PC at 1.7 GHz and possibly better with increased processing speed and/or code efficiency) and robustly. The system locates position, orientation and size of the three anatomies with an error similar to the inter-user variability, allowing physicians and sonographers to quickly navigate through ultrasound volumes of fetal heads. A large scale semantic-based fetal structure retrieval from 3DUS may be created, where the users type a semantic keyword and the system returns the structure in the volume making the 3D navigation much easier and faster.

3-D ultrasound volumes of fetal heads are automatically indexed using semantic keywords, which represent fetal anatomies. The automatic index involves the display of the correct standard plane for visualizing the requested anatomy and the biometric measurement according to the guidelines of the International Society of Ultrasound in Obstetrics and Gynecology. Anatomies are retrieved in ultrasound volumes based on semantic keywords or with or without other input. Tens of brain anatomies may be determined, even given the small, noisy, indistinct, and/or difficult to locate appearance. The principled probabilistic model combines the use of discriminative/generative classifiers with global and semi-local context.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for measuring a fetal parameter from three-dimensional ultrasound data, the method comprising:
    obtaining the three-dimensional ultrasound data representing a patient;
    applying a machine-trained classifier to the three-dimensional ultrasound data, the machine-trained classifier comprising a combination of a joint classifier for a plurality of fetal anatomies, including a first fetal anatomy, the first fetal anatomy being detected as a function of detection of a location of another fetal anatomy, and a sequence of marginal machine-trained classifiers to the three-dimensional ultrasound data, a first of the marginal machine-trained classifiers for translation of the first fetal anatomy within a volume represented by the three-dimensional ultrasound data, a second of the marginal machine-trained classifiers for rotation of the first fetal anatomy within the volume, and a third of the marginal machine-trained classifiers for scale of the first fetal anatomy within the volume, the third marginal machine-trained classifier for the scale corresponding to determining a size of the first fetal anatomy within the volume;
    detecting the first fetal anatomy as a function of the applying;
    wherein each stage in the sequence of marginal machine-trained classifiers searches through multiple locations in the three-dimensional ultrasound data to identify the locations with higher probabilities for the location of fetal anatomies and further removes false locations remaining from a previous stage in the sequence of marginal machine trained classifiers;
    wherein each of the fetal anatomies are detected by applying any numbers of degrees of freedom in the marginal machine-trained classifiers for translation, rotation and scaling;
    measuring the fetal parameter associated with the first fetal anatomy, the measuring providing a value of the fetal parameter; and
    displaying the value.

2. The method of claim 1 further comprising displaying a planar reconstruction from the three-dimensional ultrasound data, the planar reconstruction showing the fetal anatomy.

3. The method of claim 1 wherein applying comprises applying the machine-trained classifier as a detector of the fetal cerebellum, fetal cisterna magna, fetal lateral ventricles, or combinations thereof.

4. The method of claim 1 wherein applying the joint classifier comprises applying a machine-trained head detector, and then applying a machine-trained detector of the first fetal anatomy, the machine-trained detector of the first fetal anatomy dependent on an output of the machine-trained head detector.

5. The method of claim 1 wherein applying the machine-trained classifier comprises applying a first detector to first data comprising a coarse sampling of the ultrasound data and applying a second detector to second data comprising a finer sampling of the same ultrasound data, the second detector searching for the first fetal anatomy in the ultrasound data, a search space of less than all the ultrasound data by the second detector being a function of an output of the first detector.

6. The method of claim 1 wherein applying the machine-trained classifier comprises applying a probabilistic boosting tree.

7. The method of claim 1 wherein measuring comprises determining a line representing the first fetal anatomy as an output of the machine-trained classifier, determining a voxel size associated with the ultrasound data, and calculating a distance of the first fetal anatomy as a function of the line and the voxel size.

8. In a non-transitory computer readable storage medium having stored therein data representing instructions executable by a programmed processor for measuring a fetal parameter from three-dimensional ultrasound data, the storage medium comprising instructions for:
    obtaining the three-dimensional ultrasound data representing a patient; receiving user input requesting automatic measurement of a fetal head anatomy, the fetal parameter being for the fetal head anatomy;
    detecting the fetal head anatomy with a computer learnt classifier, the computer learnt classifier operable to detect from the three-dimensional ultrasound data without user indication of a position, the computer learnt classifier comprising both a joint classifier such that the fetal head anatomy is detected as a function of a location of other anatomy and a marginal space classifier including classification of a size of the fetal head anatomy, wherein each stage in a sequence of the marginal machine-trained classifier searches through multiple locations in the three-dimensional ultrasound data to identify locations with higher probabilities for the location of the fetal head anatomy and further removes false locations remaining from a previous stage in the sequence of the marginal machine trained classifier, wherein the fetal anatomy is detected by applying any numbers of degrees of freedom in the marginal machine-trained classifier for translation, rotation and scaling; and
    calculating a value for the fetal parameter.

9. The non-transitory computer readable storage medium of claim 8 wherein detecting comprises detecting a fetal head with a first probabilistic boosting tree classifier, and detecting a cerebellum, cisterna magna, lateral ventricle or combinations thereof as the fetal head anatomy using a second probabilistic boosting tree classifier.

10. The non-transitory computer readable storage medium of claim 8 wherein detecting with the marginal space classifier comprises using a translation search with a first detector of the computer learnt classifier, detecting using a scale search limited by a position output by the first detector with a second detector of the computer learnt classifier, and detecting using an orientation search limited by a scale output by the second detector and the position with a third detector of the computer learnt classifier.

11. The non-transitory computer readable storage medium of claim 8 wherein detecting comprises detecting with detectors trained for different resolutions of the ultrasound data in a volume pyramid.

12. The non-transitory computer readable storage medium of claim 8 wherein detecting comprises detecting a fetal head, cerebellum, cisterna magna, and lateral ventricles with a joint, hierarchal, marginal space classifier.

13. A system for measuring a fetal parameter from three-dimensional ultrasound data, the system comprising:
   a memory operable to store ultrasound data representing a fetal volume;
   a processor operable to apply a probabilistic model to detect a first anatomy as a function of the ultrasound data and as a function of a position of a second anatomy, the detection of the first anatomy being performed sequentially in a sequence of stages of position of the first anatomy, orientation of the first anatomy, and scale of the first anatomy, the scale comprising a size of the first anatomy in the fetal volume, wherein each stage in the sequence searches through multiple locations in the ultrasound data to identify locations with higher probabilities for a location of the first anatomy and further removes false locations remaining from a previous stage in the sequence, wherein the first anatomy is detected by applying any numbers of degrees of freedom in the probabilistic model for position, orientation and scale; and
   a display operable to display an image of the first anatomy, a value representing a measurement of the first anatomy or combinations thereof.

14. The system of claim 13 wherein the probabilistic model comprises a machine learned classifier.

15. The system of claim 14 wherein the second anatomy comprises a fetal skull, the first anatomy comprises a cerebellum, a cisterna magna, or a lateral ventricle.

* * * * *